(12) United States Patent
Boyden et al.

(10) Patent No.: US 8,910,638 B2
(45) Date of Patent: Dec. 16, 2014

(54) METHODS AND APPARATUS FOR HIGH-THROUGHPUT NEURAL SCREENING

(75) Inventors: Edward Boyden, Chestnut Hill, MA (US); Jacob Bernstein, Cambridge, MA (US); Christian Wentz, Cambridge, MA (US); Giovanni Talei Franzesi, Boston, MA (US); Michael Baratta, Boulder, CO (US); Brian Allen, Cambridge, MA (US); Anthony Zorzos, Cambridge, MA (US); Jorg Scholvin, Boston, MA (US); Clifton Fonstad, Arlington, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 332 days.

(21) Appl. No.: 13/280,229

(22) Filed: Oct. 24, 2011

(65) Prior Publication Data

US 2012/0089205 A1 Apr. 12, 2012

Related U.S. Application Data

(63) Continuation-in-part of application No. 12/843,587, filed on Jul. 26, 2010, now Pat. No. 8,545,543, which is a continuation-in-part of application No. 12/714,436, (Continued)

(51) Int. Cl.
*A61B 19/00* (2006.01)
*A61N 5/06* (2006.01)
*F21V 8/00* (2006.01)
*G02B 6/125* (2006.01)

(52) U.S. Cl.
CPC ............ *A61N 5/0601* (2013.01); *A61N 5/0622* (2013.01); *G02B 6/0008* (2013.01);

(Continued)

(58) Field of Classification Search
CPC .............. A61N 5/0622; A61N 1/3605; A61N 1/36057; A61N 1/36082; A61N 1/0529; A61N 1/0531; A61N 1/0534; A61N 2005/0626; A61N 2005/063; A61N 2005/0639; A61N 2005/067; A61N 2005/0652
USPC ............... 607/88–93, 115, 116, 118; 128/898
See application file for complete search history.

(56) References Cited

U.S. PATENT DOCUMENTS 7,444,877 B2   11/2008   Li et al.
8,475,506 B1 *  7/2013   Bendett et al. ................. 607/89

(Continued)

FOREIGN PATENT DOCUMENTS

WO   WO2010056970 A2   5/2010

OTHER PUBLICATIONS

Poher, V., et al. (2008). Micro-LED arrays: a tool for two-dimensional neuron stimulation. 2008 Journal of Physics D: Applied Physics 41, 094014.

(Continued)

*Primary Examiner* — Ahmed Farah
(74) *Attorney, Agent, or Firm* — Stephen R. Otis

(57) ABSTRACT

In exemplary implementations of this invention, high-throughput screening of a mammalian brain is performed to locate neural circuit targets of interest. A variety of search patterns may be used for this neural screening, including (a) iterative subdivision, (b) serial search, and (c) combinatorial. To perform this neural screening, an array of optical fibers (or an array of waveguides) is inserted into the brain. Alternately, the array is positioned adjacent to the brain. Each fiber or waveguide in the array is coupled to a light source (LED or laser). The brain has been previously sensitized to light, using genetically encoded optical neural control reagents, which are delivered either using viruses or via transgenic means. In the screening, the array is used to optically perturb the brain. For example, the neurons of the brain may be activated by one color of light, and/or silenced by another color of light.

8 Claims, 12 Drawing Sheets

Related U.S. Application Data filed on Feb. 26, 2010, now abandoned, which is a continuation-in-part of application No. 12/355,745, filed on Jan. 16, 2009, which is a continuation-in-part of application No. 12/118,673, filed on May 9, 2008, now abandoned.

(60) Provisional application No. 61/405,977, filed on Oct. 22, 2010, provisional application No. 61/412,954, filed on Nov. 12, 2010, provisional application No. 61/413,161, filed on Nov. 12, 2010, provisional application No. 61/413,431, filed on Nov. 13, 2010, provisional application No. 61/249,714, filed on Oct. 8, 2009, provisional application No. 60/917,055, filed on May 9, 2007, provisional application No. 61/021,612, filed on Jan. 16, 2008, provisional application No. 61/155,855, filed on Feb. 26, 2009.

(52) U.S. Cl.
CPC ............... *G02B 6/125* (2013.01); *A61N 5/062* (2013.01); *A61N 2005/0612* (2013.01); *A61N 2005/063* (2013.01); *A61N 2005/0651* (2013.01)
USPC ............................. 128/898; 607/88; 607/92

(56) References Cited

U.S. PATENT DOCUMENTS

| | | | |
|---|---|---|---|
| 8,545,543 B2* | 10/2013 | Zorzos et al. | 607/89 |
| 8,696,722 B2* | 4/2014 | Deisseroth et al. | 607/80 |
| 2005/0202398 A1 | 9/2005 | Hegemann et al. | |
| 2006/0129210 A1 | 6/2006 | Cantin et al. | |
| 2006/0155348 A1* | 7/2006 | deCharms | 607/89 |
| 2007/0060984 A1* | 3/2007 | Webb et al. | 607/89 |
| 2007/0261127 A1 | 11/2007 | Boyden et al. | |
| 2008/0249517 A1 | 10/2008 | Svanberg | |
| 2009/0054954 A1 | 2/2009 | Foley et al. | |
| 2009/0099038 A1 | 4/2009 | Deisseroth et al. | |
| 2009/0221921 A1 | 9/2009 | Cottrell et al. | |
| 2010/0145418 A1 | 6/2010 | Zhang et al. | |
| 2011/0125077 A1 | 5/2011 | Denison et al. | |
| 2013/0102833 A1* | 4/2013 | John et al. | 600/13 |
| 2013/0289676 A1* | 10/2013 | Deisseroth et al. | 607/92 |

OTHER PUBLICATIONS

Xu, H., et al., (2008). Application of blue-green and ultraviolet micro-LEDs to biological imaging and detection. Journal of Physics D: Applied Physics 41 094013.

Bernstein, J., et al., (2008) Prosthetic systems for therapeutic optical activation and silencing of genetically-targeted neurons, Proc Soc Photo Opt Instrum Eng. 2008; 6854: 68540H.

Boyden, E., et al. (2005). Millisecond-timescale, genetically targeted optical control of neural activity. Nat Neurosci 8 (9): 1263-1268.

Chow, B., et al. (2010). High-performance genetically targetable optical neural silencing by light-driven proton pumps. Nature 463(7277): 98-102.

Han, X., et al., (2007). Multiple-color optical activation, silencing, and desynchronization of neural activity, with single-spike temporal resolution. PLoS ONE 2: e299.

Zhang, F., et al. (2006). "Channelrhodopsin-2 and optical control of excitable cells." Nat Methods 3(10): 785-792.

Hildebrant, V., et al., (1993) Bacteriorhodopsin expressed in *Schizosaccharomyces pombe* pumps protons through the plasma membrane. Proc. Natl. Acad. Sci. USA, vol. 90, pp. 3578-3582, Apr. 1993.

Mukohata, Y., et al., (1999) Halobacterial rhodopsins. J. Biochem. Apr. 1999, 124(4): 649-57.

Dittgen, T., et al., (2004) *Lentivirus*-based genetic manipulations of cortical neurons and their optical and electrophysiological monitoring in vivo. Proc Natl Acad Sci U S A. Dec. 28, 2004; 101(52): 18206-18211.

Wang. H., et al. (2007) High-speed mapping of synaptic connectivity using photostimulation in Channelrhodopsin-2 transgenic mice. Proceedings of the National Academy of Sciences of the United States of America, May 2007, vol. 104, Issue 19, pp. 8143-8148.

Zhang, F., et al., (2008) Red-shifted optogenetic excitation: a tool for fast neural control derived from *Volvox carteri*. Nature Neuroscience, 2008, pp. 631-633, vol. 11, No. 6.

Walter, J., et al., (2007), Light-powering *Escherichia coli* with proteorhodopsin. Proc. Nat. Acad. Sci. (PNAS), Feb. 13, 2007, pp. 2408-2412, vol. 104, No. 7, The National Academy of Sciences of the USA, USA.

Han, X., et al., (2009) Millisecond-Timescale Optical Control of Neural Dynamics in the Nonhuman Primate Brain. Neuron, 62, 191-198, Apr. 20, 2009.

\* cited by examiner

METHODS AND APPARATUS FOR HIGH-THROUGHPUT NEURAL SCREENING

RELATED APPLICATIONS

This application is a continuation-in-part of pending U.S. application Ser. No. 12/118,673, filed May 9, 2008, published Dec. 11, 2008 as Publication No. US 2008-0306576 A1 titled "Optical Cell Control Prosthetics", which claims the benefit of U.S. provisional application Ser. No. 60/917,055, filed May 9, 2007, the entire disclosures of which are herein incorporated by reference.

This application is a continuation-in-part of pending U.S. application Ser. No. 12/355,745, filed Jan. 16, 2009, published Aug. 20, 2009 as Publication No. US 2009-0210039 A1, titled "Prosthetic system for therapeutic optical activation and silencing of genetically-targeted neurons", which claims the benefit of U.S. provisional application Ser. 61/021,612, filed Jan. 16, 2008, the entire disclosures of which are herein incorporated by reference.

This application is a continuation-in-part of pending U.S. application Ser. No. 12/714,436, filed Feb. 26, 2010, published Jul. 7, 2011 as Publication No. US 2011-0165681 A1 titled "Light-Activated Proton Pumps and Applications Thereof", which claims the benefit of U.S. Provisional Application Ser. No. 61/155,855, filed Feb. 26, 2009, the entire disclosures of which are herein incorporated by reference This application is a continuation-in-part of pending U.S. application Ser. No. 12/843,587, filed Jul. 26, 2010, published Apr. 14, 2011 as Publication No. US 2011-0087311 A1, titled "Methods and Apparatus for Microstructure Lightguides", which claims the benefit of U.S. Provisional Application Ser. No. 61/249,714, filed Oct. 8, 2009, the entire disclosures of which are herein incorporated by reference.

This application claims the benefit of U.S. Provisional Application Ser. No. 61/412,954, filed Nov. 12, 2010, the entire disclosure of which is herein incorporated by reference.

This application claims the benefit of U.S. Provisional Application Ser. No. 61/413,161, filed Nov. 12, 2010, the entire disclosure of which is herein incorporated by reference.

This application claims the benefit of U.S. Provisional Application Ser. No. 61/413,431, filed Nov. 13, 2010, the entire disclosure of which is herein incorporated by reference.

This application claims the benefit of U.S. Provisional Application Ser. No. 61/405,977, filed Oct. 22, 2010, the entire disclosure of which is herein incorporated by reference.

As used herein, the "Prior Applications" means the patent applications listed above.

STATEMENT REGARDING FEDERALLY SPONSORED RESEARCH OR DEVELOPMENT

This invention was made with U.S. government support under National Institute of Health grants 1RC1MH088182, 1R01NS067199, and 1R43NS070453, under National Institute of Health's New Innovator Award DP2OD002002, and under National Science Foundation grants 0835878 and 0848804. The government has certain rights in this invention.

FIELD OF THE TECHNOLOGY

The present invention relates generally to screening of neural tissue using optical neural control reagents.

SUMMARY

In exemplary implementations of this invention, high-throughput screening of a mammalian brain is performed to locate neural circuit targets of interest. A variety of search patterns may be used for this neural screening, including (a) iterative subdivision, (b) serial search, and (c) combinatorial.

To perform this neural screening, an array of optical fibers or an array of waveguides is inserted into the brain, or positioned adjacent to the brain. Each fiber or waveguide in the array is coupled to a light source (LED or laser). The array comprises N fibers or waveguides (numbered 1, 2, ... N). The brain has been previously sensitized to light, using genetically encoded optical neural control reagents, which are delivered either using viruses or via transgenic means. In the screening, the array is used to optically perturb the brain. For example, the neurons of the brain may be activated by one color of light, and/or silenced by another color of light.

In some implementations, the neural screening is done by iterative subdivision using optical silencing. For example, this iterative subdivision may be performed as follows: A subset of the N optical devices is turned on, thus delivering light via the corresponding fibers or waveguides to a set of three-dimensionally distributed sites throughout the brain. For example, the devices coupled to the fibers or waveguides numbered a1, a2, . . . an may be turned on. These fibers or waveguides may collectively tile an entire brain structure, say the cortex, or hippocampus.

In this example of iterative subdivision, the screening begins by optically silencing the entire brain structure. Measurements are taken to see if an effect is observed (e.g., electrophysiological measurements may be taken to determine if there is an improvement in the brain disorder state of an animal model of epilepsy or depression). If the effect is observed, then half of the structure is silenced, by turning on the devices a1, a2, . . . a(n/2) and then the other half of the structure is silenced by turning on devices n/2+1), a(n/2+2), . . . a(n), in two successive experiments. Suppose that turning on devices a1, a2, . . . a(n/2) shows an effect, but turning on the other set of devices does not. This indicates that the neural circuit targets are found within the regions targeted by devices a1, a2, . . . a(n/2). The set of devices is then subdivided again in half, and the process repeated iteratively, honing in on a precise neural target within the brain, in log(n) steps.

Alternately, the neural screening is done by serial search, rather than iterative subdivision. In a serial search, each site in the brain structure is optically perturbed, one site at a time, finding the key area in O(n) steps. This may be a better way to screen, if multiple sites may have interactions. In a serial search, the optical perturbation of neural circuit targets may comprise optical activation (e.g., for the entire serial search) or optical silencing (e.g., for the entire serial search). Measurements (e.g., electrophysiological measurements) are taken after each step, to see if an effect is observed.

Alternately, the neural screening may be done in a combinatorial pattern. This may be particularly useful after key sites are found by one of the above search patterns. For example, suppose that, by using the iterative subdivision or serial search approach, it is determined that a(1), a(5), and a(7) each show an effect. These sites can then be combinatorially screened to see if synergies emerge, or whether the sites occlude. For example, in combinatorial screening, combinations of such sites may be activated or silenced. At each step, measurements are taken to see if an effect is observed. A combinatorial screening may, for example, help indicate whether the neural targets are additive in function.

Advantageously, these search patterns may be used for high throughput screening of many neural circuit targets in the brain, In a high throughput circuit screen, it is preferable that both the optical perturbation (e.g. optical silencing or optical activation) and the measurements are precisely repeated. The methods of readout may, for example, be behavioral, electrophysiological (e.g., a given neuron fires an electrical potential), or imaging (e.g., an fMRI brain signature). Preferably, the neural perturbation should minimally impact the neural circuit's functions.

An electrophysiological readout is well-suited for high-throughput neural screening. For example, in a serial search using optical activation, the search pattern may proceed through the entire brain structure, activating sites one by one, to see which trigger an electrophysiological response that is known to be indicative of, say, sleep state, positive emotion, or other desired effect. Such electrophysiological proxies for behavior are useful, if they are realistic and predictive proxies, because behavior can take a long time, and behaviors are sometimes hard to interpret, whereas neural circuits known to be involved with specific phenomena can be rapidly measured, and unambiguously interpreted.

A high-throughput neural screen can be done across many animal brains at once, in order to speed up the search with parallelization. In some implementations, a wireless neural control device is used to facilitate high-throughput assessment. These wireless devices may be cheap, capable of delivering light across the (thinned) skull, and capable of being remotely from a single computer by a single operator.

The targets identified by the neural screen can serve as novel drug targets. In this case, pharmaceuticals can be identified that affect the targets identified at the neural circuit level, through traditional molecular screens.

Also, the sites in the brain that were identified by the neural screen can serve as novel targets for neuromodulation (e.g., through electrical, magnetic, ultrasonic, or other kinds of stimulation).

The above description of the present invention is just a summary. It is intended only to give a general introduction to some illustrative implementations of this invention. It does not describe all of the details of this invention. This invention may be implemented in many other ways.

Figure 1:
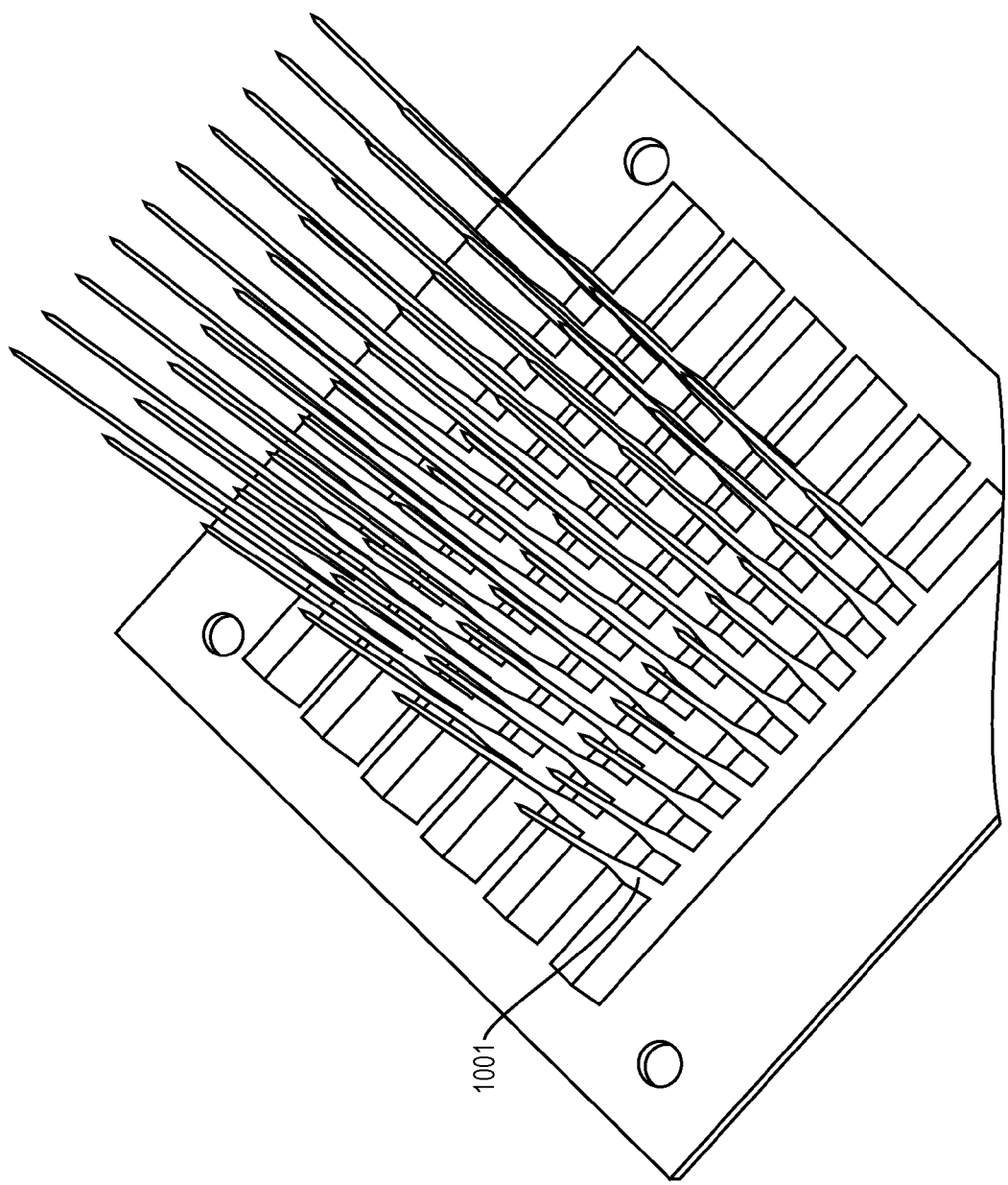
FIG. 1 is a perspective view of an array of light probes.

The above Figures illustrate some illustrative implementations of this invention, or provide information that relates to those implementations. However, this invention may be implemented in many other ways. The above Figures do not show all of the details of this invention.

DETAILED DESCRIPTION

Some Definitions

First, some definitions and clarifications. As used herein::

"Neural control technology" means one or more of the methods and apparatus (e.g., arrays of light fibers, arrays of microfabricated lightguides, and techniques of optical perturbation using optical neural control reagents) that are described in the Prior Applications.

To "silence" a neural target means to decrease the electrical activity of the set of neurons that comprises the target. Normally neurons fire action potentials, and exhibit subthreshold activity as well; silencing a target means to decrease, perhaps to zero, the number of action potentials fired by, or the electrical voltage of, the cells in the target. The target may be defined anatomically, functionally, molecularly, or otherwise (e.g., a set of neurons within a region, or distributed throughout the brain, that expresses a given molecule, or that is overactive in a given disease, or that responds to a given drug, or that projects from one region to another).

To "optically silence" a neural target means to silence the neural target by optical perturbation.

To "activate" a neural target means to increase the electrical activity of the set of neurons that comprises the target. Normally neurons fire action potentials, and exhibit subthreshold activity as well; activating a target means to increase, perhaps to a high rate, the number of action potentials fired by a cell, or the electrical voltage of the cells, in the target. The target may be defined anatomically, functionally, molecularly, or otherwise (e.g., a set of neurons within a region, or distributed throughout the brain, that expresses a given molecule, or that is overactive in a given disease, or that responds to a given drug, or that projects from one region to another).

To "optically activate" (or "optically activate") a neural target means to activate the neural target by optical perturbation.

A "measurement" includes a measurement by a sensor, or an observation by a human being. For example, the term "measurement" includes any method of readout, including behavioral, electrophysiological (e.g., a given neuron fires an electrical potential), or imaging (e.g., PET or fMRI).

The term "optical probe" includes an optical fiber, a waveguide, a probe that comprises multiple waveguides, or an array of any one or more of the above, including (a) an array of optical fibers or (b) an array of probes, which probes each comprise multiple waveguides.

The term "include" shall be construed broadly, as if followed by "without limitation".

The term "or" is an inclusive disjunctive. For example "A or B" is true if A is true, or B is true, or both A or B are true.

The above definitions and clarifications of terms apply to all grammatical variations of those terms.

Details

As described in the Prior Applications, neural control technology may be used to silence or activate neural circuit targets. In an illustrative example, a mammalian brain is sensitized to light, using genetically encoded optical neural control reagents, which are delivered either using viruses or via transgenic means. An array of lightguides (e.g., optical fibers or microfabricated waveguides) is inserted into the brain, or positioned adjacent to the brain. Each lightguide is coupled to a light source (e.g., LED or laser). Using this array of lightguides, the brain is optically perturbed. For example, the neurons of the brain may be activated by one color of light, and/or silenced by another color of light.

In illustrative implementations of this invention, neural control technology is employed in high-throughput screening, in order to locate neural circuit targets of interest.

The neural circuit targets may be defined by specific neuroanatomical boundaries, cell types, pathways, or activity patterns.

A variety of search patterns may be used for neural screening, including iterative subdivision, serial search and combinatorial.

A neural screen by iterative subdivision may be performed as follows: neural control technology is used to silence an entire brain structure. Measurements are taken to see if this produces a defined outcome. If it does, neural control technology is used to optically silence subdivisions of the brain structure, one subdivision at a time. (Generally, it is preferable for these subdivisions to be halves of the entire structure. However, other subdivisions, such as thirds, or fourths, and so on, or subdivisions of unequal size or varying shapes may be appropriate, in particular circumstances). Measurements are taken again, to see for which subdivisions this produces a defined outcome. The process is repeated iteratively for progressively smaller and smaller subdivisions of the brain structure, until one or more neural targets of interest are identified.

Alternately, optical activation (rather than optical silencing) may be used for neural screening by iterative subdivision. In some cases, it may be advantageous to do so. Generally, however, it is preferable to use optical silencing when screening by iterative subdivision, because in most cases it does not make sense to optically activate an entire brain structure.

A neural screen by serial search may be performed as follows: neural control technology is used to optically activate all of the areas in a brain region (such as a particular brain structure, or even the entire brain), one area at a time. For each area, measurements are taken to determine if a defined outcome occurs. Thus, the serial search identifies neural targets of interest (i.e., the targets for which the defined outcome occurs). Alternately, a serial search may be performed using optical silencing, rather than optical activation.

Once some neural targets have been identified (e.g., by iterative subdivision or serial search), it may be advantageous to perform a combinatorial neural screening.

A combinatorial neural screen may be performed as follows: neural control technology may be used to simultaneously optically perturb different regions in the brain. For example, multiple neural targets may simultaneously be silenced, or simultaneously activated. Observations are taken to see if this optical perturbation of a combination of targets produces a defined outcome.

A combinatorial screen of multiple sites may be performed to determine, for example, if synergies emerge, or whether the sites occlude. For example, in combinatorial screening, combinations of such sites may be activated or silenced. A combinatorial screening may, for example, help indicate whether the neural targets are additive in function.

In a combinatorial screen, the optical perturbation that is delivered to the different targets may consist of a single stimulus, or may instead comprise a pulse sequence or other sequence of stimuli. In any case, it is usually preferable to repeat the perturbation (either a single stimuli or sequence of stimuli) in order to take multiple observations.

In exemplary implementations of a combinatorial screen, the type and timing of the optical perturbation is the same for each of the targets. However, many variants may be used, and may be appropriate in particular circumstances. For example, in a combinatorial screen, the type of optical perturbation may differ between the different targets. For example, some targets may be optically activated at the same time as others are optically silenced. Or, for example, stimuli may be given to different targets within the combination at different times or in different sequences.

In some implementations of the search patterns discussed above (iterative subdivision, serial search and combinatorial), the subdivisions that are investigated are defined simply by dividing a larger volume that is being screened into a set of smaller subvolumes, that together comprise all of the larger volume. In other implementations, however, a more selective approach to subdivision is taken. For example, the subdivisions screened may comprise only subvolumes that contain a certain cell type, or certain neural pathway, or certain neural features believed to responsible for certain activity patterns. In that case, other subvolumes, which do not contain such items, are not screened, even though they are located within the larger volume.

In illustrative implementations, high-throughput screening involves independent activation or silencing of multiple neural circuit elements, on the millisecond timescale, coupled with appropriate methods of reading out the response of neural circuits to optical modulation.

In illustrative implementations, multisite optical modulation is be used to: (a) rapidly screen many neural circuit elements to determine which elements are involved in a particular behavior or neural computation, (b) probe the consequences of interactions between circuit elements which cannot be predicted from the response of each element to independent perturbation, and (c) address large brain structures (e.g. the hippocampus) which extend beyond the volume of neural tissue which can be activated by a single light source in the brain (without emitting so much power from the light source that detrimental heating of tissue occurs).

FIG. 1 is a perspective view of an array of light probes, which may be used for neural screening.

Figure 2A:
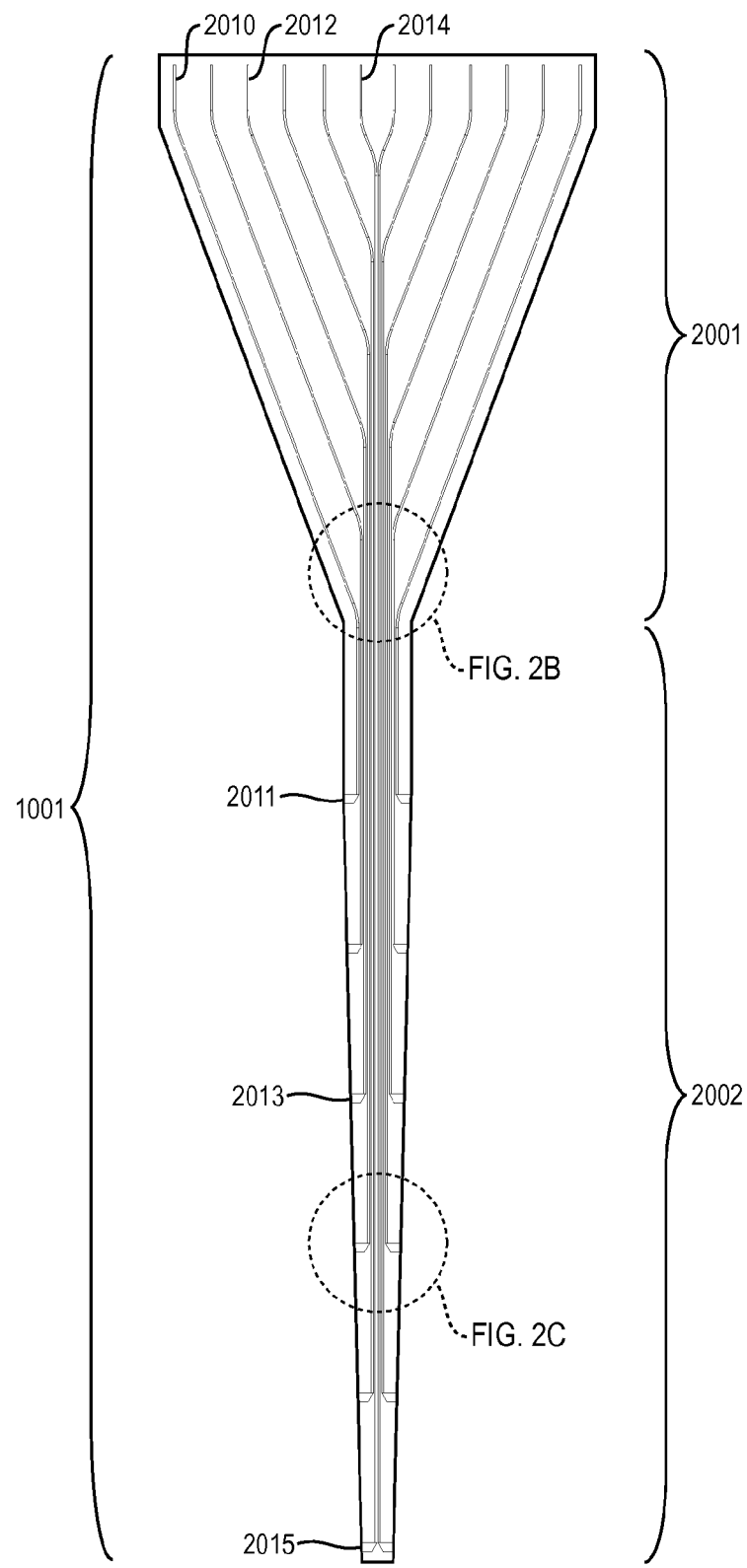
FIG. 2A is a diagram of one of the probes in the array. The probe includes multiple optical waveguide channels.

FIG. 2A is a diagram of one of the probes 1001 in the array. The probe includes multiple optical waveguide channels. The probe comprises an area for light input 2001 and a shank 2002. Light entering a waveguide exits at an aperture in the shank. For example, light entering waveguides 2010, 2012 and 2014 exits the shank apertures 2011, 2013 and 2015, respectively.

Figure 2B:
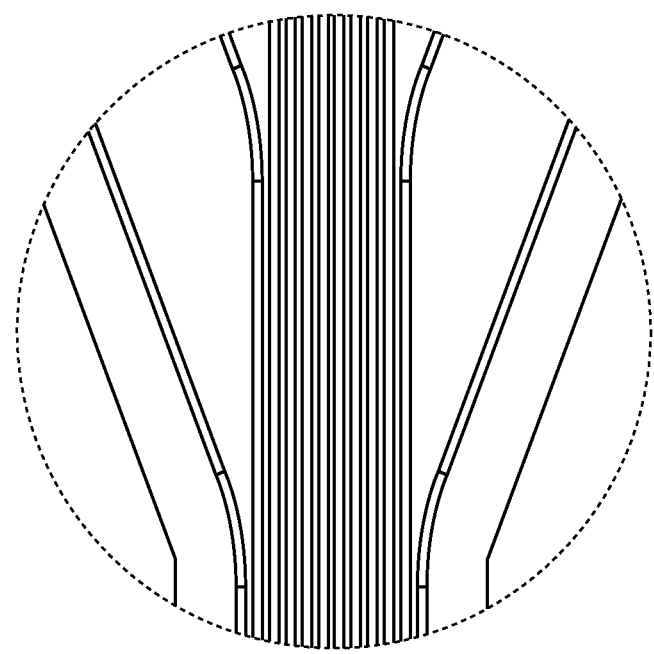
FIG. 2B is a detailed view of a portion of the probe in FIG. 2A, showing waveguide channels coming closer together near the top of the shank of the probe.

FIG. 2B is a detailed view of a portion of the probe in FIG. 2A, showing waveguide channels coming closer together near the top of the shank of the probe.

Figure 2C:
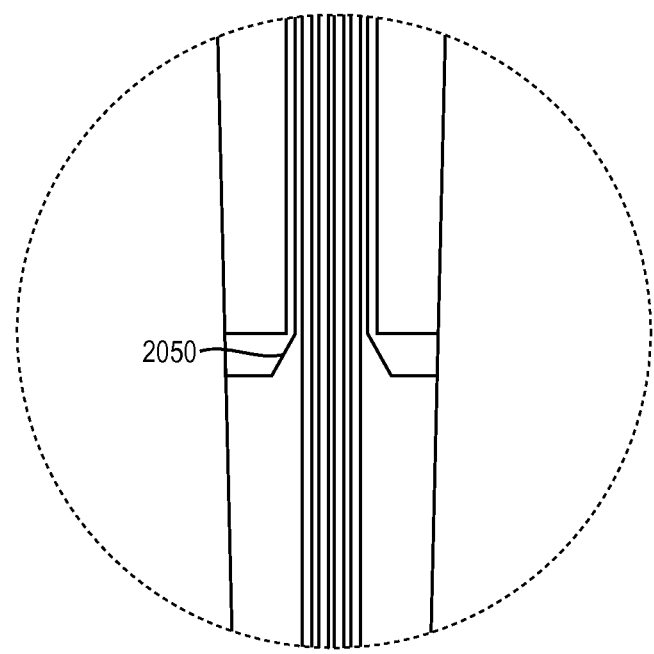
FIG. 2C is a detailed view of a portion of the shank of the probe in FIG. 2A, showing apertures where light from two waveguide channels can exit the shank.

FIG. 2C is a detailed view of a portion of the shank of the probe in FIG. 2A, showing apertures where light from two waveguide channels can exit the shank. At each aperture, a corner mirror (e.g., 2050), directs light from the waveguide out of the shank.

Figure 2D:
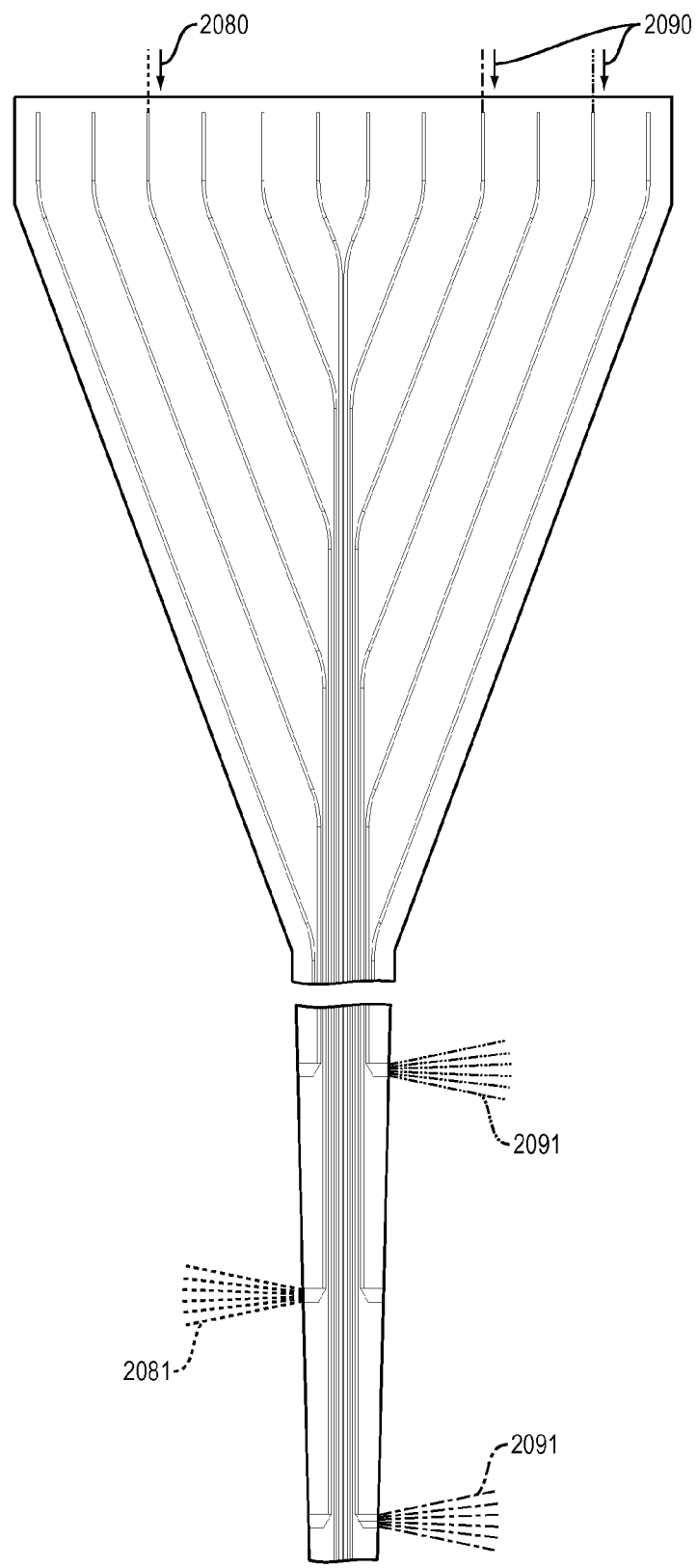
FIG. 2D shows a probe that is simultaneously delivering two different colors of light. The two colors of light travel along different waveguides to different apertures along the shank of the probe.

FIG. 2D shows a probe that is simultaneously delivering two different colors of light. The two colors of light travel along different waveguides to different apertures along the shank of the probe. In this example, one color of light (2080) enters a waveguide and exits the shank at one location (2081), and another color of light 2090 enters two different waveguides and exits the shank at two locations (2091).

Figure 2E:
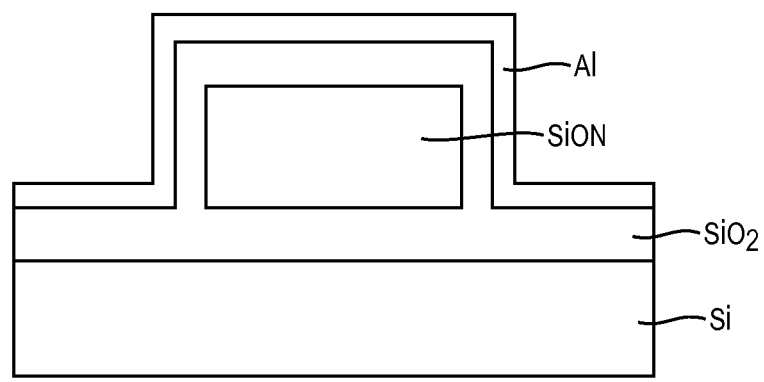
FIG. 2E is a diagram of cross-section of a waveguide in the probe.

FIG. 2E is a diagram of cross-section of a waveguide in the probe.

Figure 3:
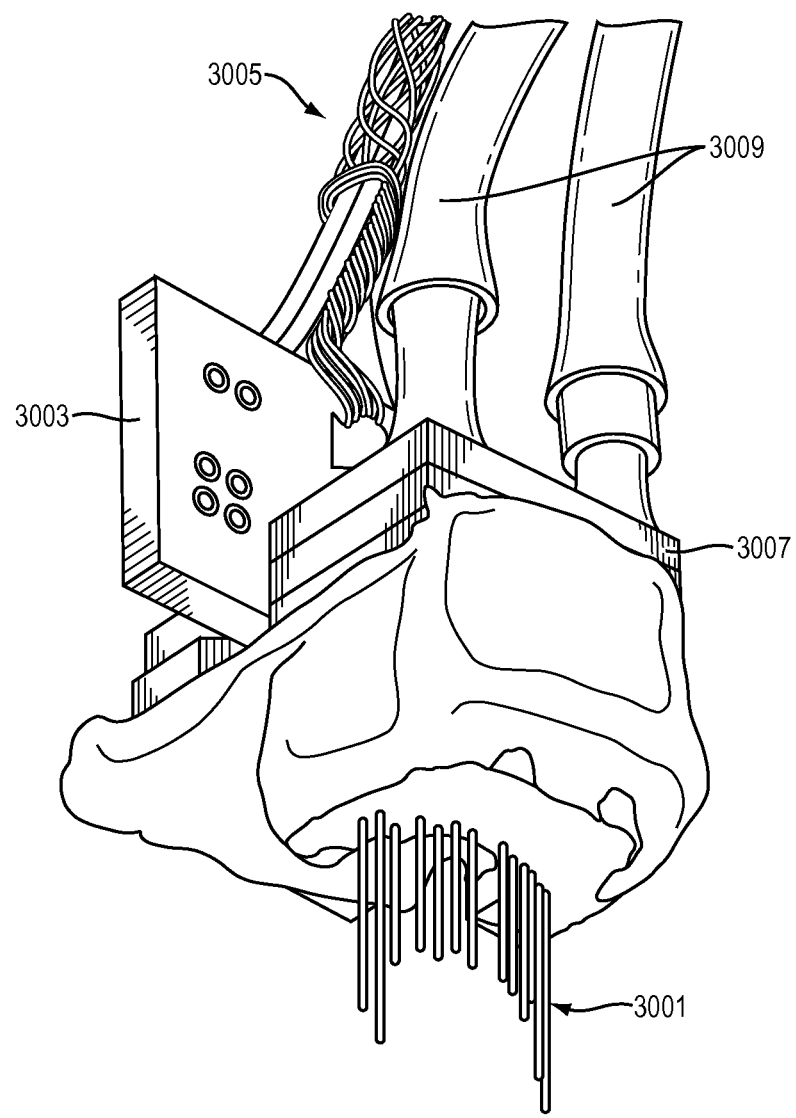
FIG. 3 is a perspective view of an optical fiber array with a cooling unit and wired power supply.

FIG. 3 is a perspective view of an array with a cooling unit and wired power supply. Optical fibers 3001 point down. A cooling unit 3007 is supplied with coolant by intake and outtake tubes 3009. Wires 3005 provide a power supply for the light sources and a circuit board 3003.

Figure 4A:
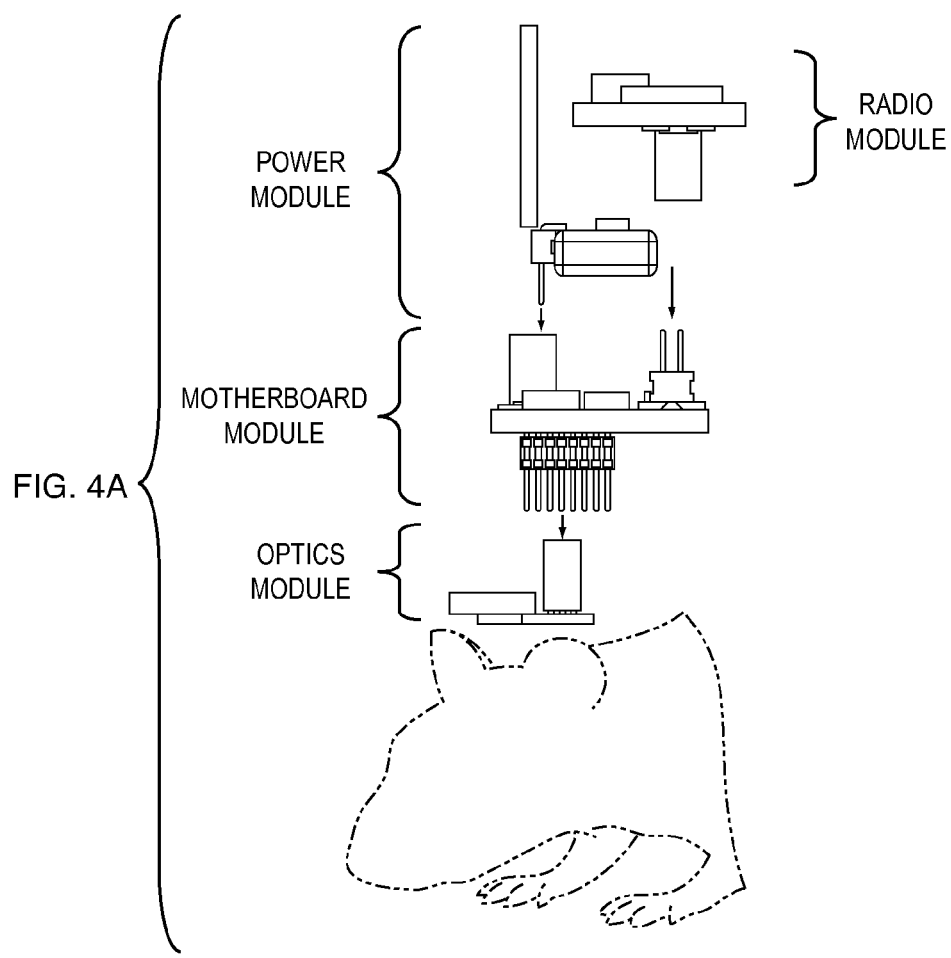
FIG. 4A is a high-level diagram of hardware in a probe array with a RF power source.

FIG. 4A is a high-level diagram of hardware in a probe array with a RF power source.

Figure 4B:
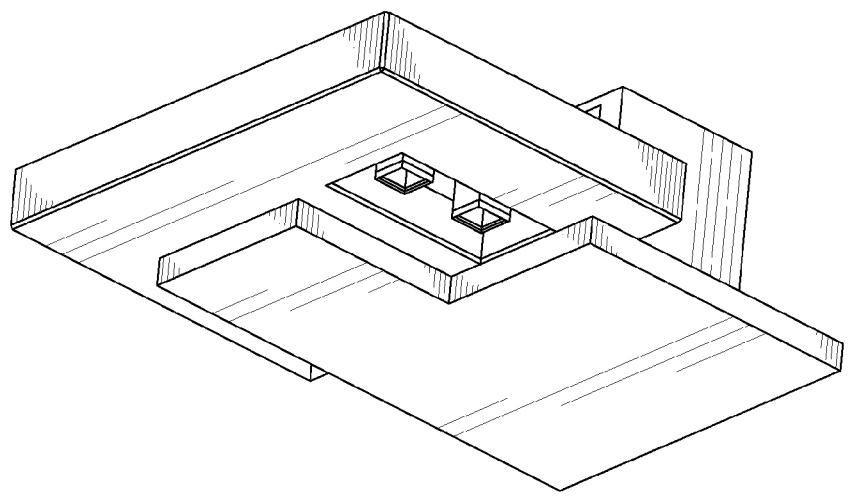
FIG. 4B is a perspective view of the underside of an optics module in a probe array with a RF power source.

FIG. 4B is a perspective view of the underside of an optics module in a probe array with a RF power source.

Figure 5:
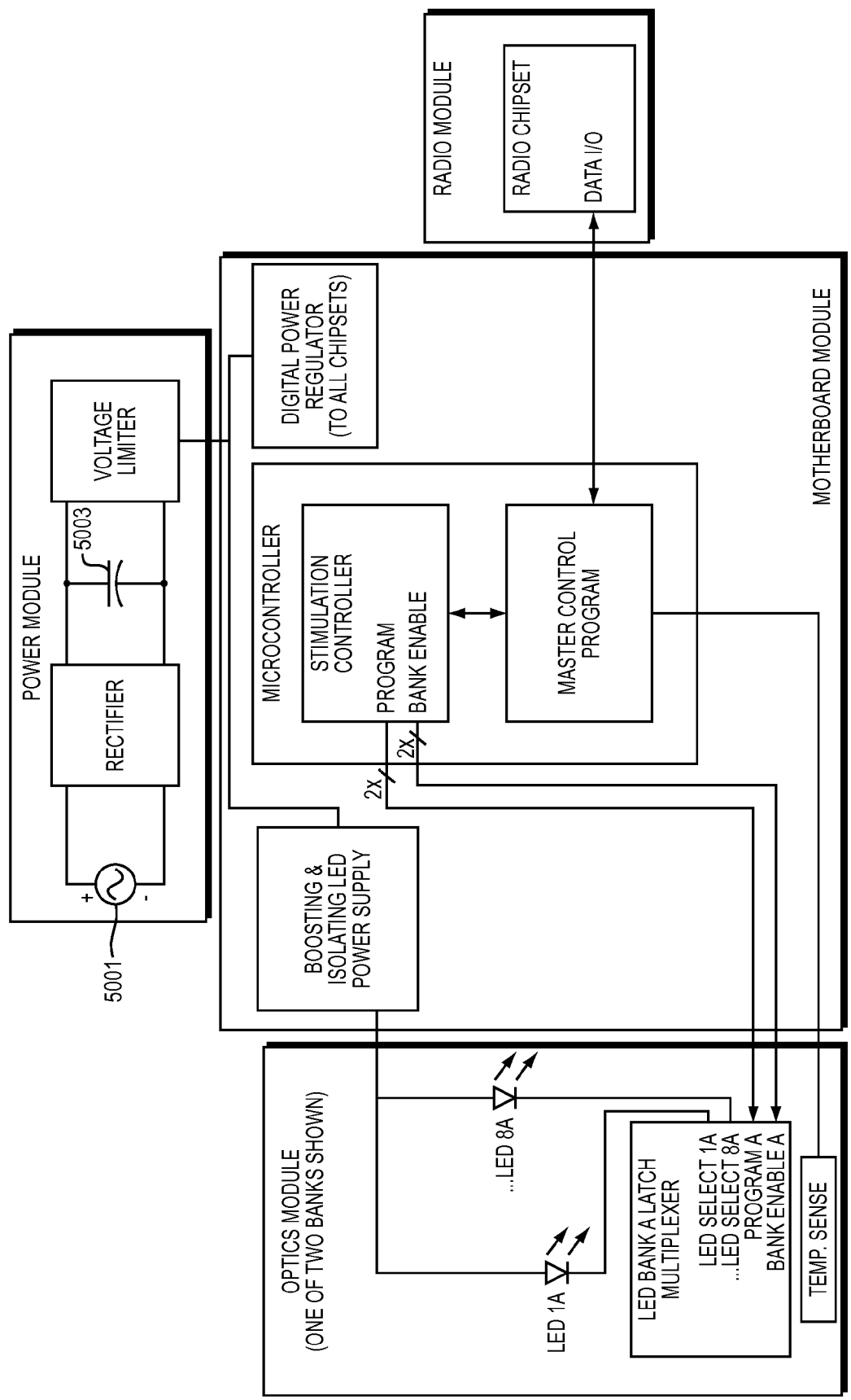
FIG. 5 is a high-level schematic of a probe array with a RF power source.

FIG. 5 is a high-level schematic of a probe array with a RF power source. The power module of the array includes a power antenna 5001 and a supercapacitor 5003.

It must be stressed that this invention is not limited to any particular implementation of a lightguide array. For example, single probes constituting a lightguide array of microfabricated waveguides may be used to address many circuit elements in one vertical column of neural tissue, and maybe be arranged in a 2-D array to achieve full 3-D optical addressability of neural circuit elements.

Figure 6:
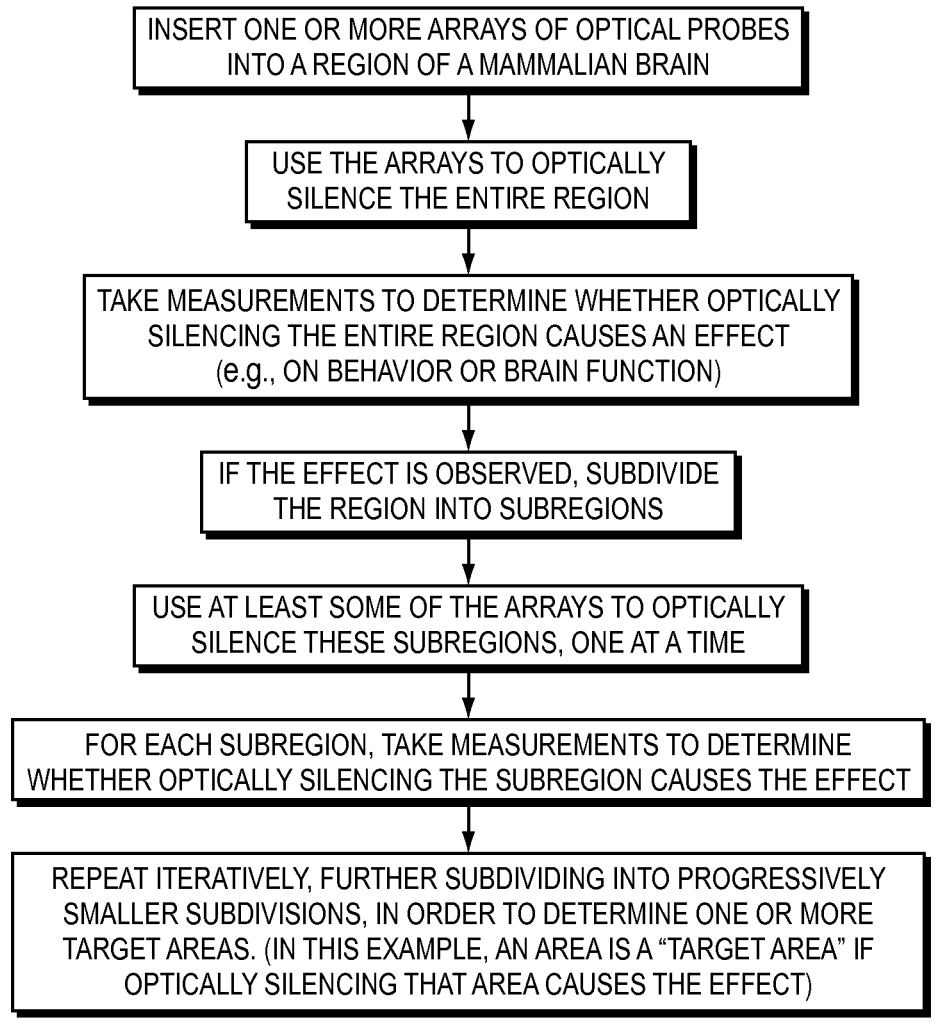
FIG. 6 is a flow-chart of an iterative method of neural screening, in which progressively smaller subdivisions of a region of the brain are optically silenced.

FIG. 6 is a flow-chart of an iterative method of neural screening, in which progressively smaller subdivisions of a region of the brain are optically silenced, to find a neural target.

Figure 7:
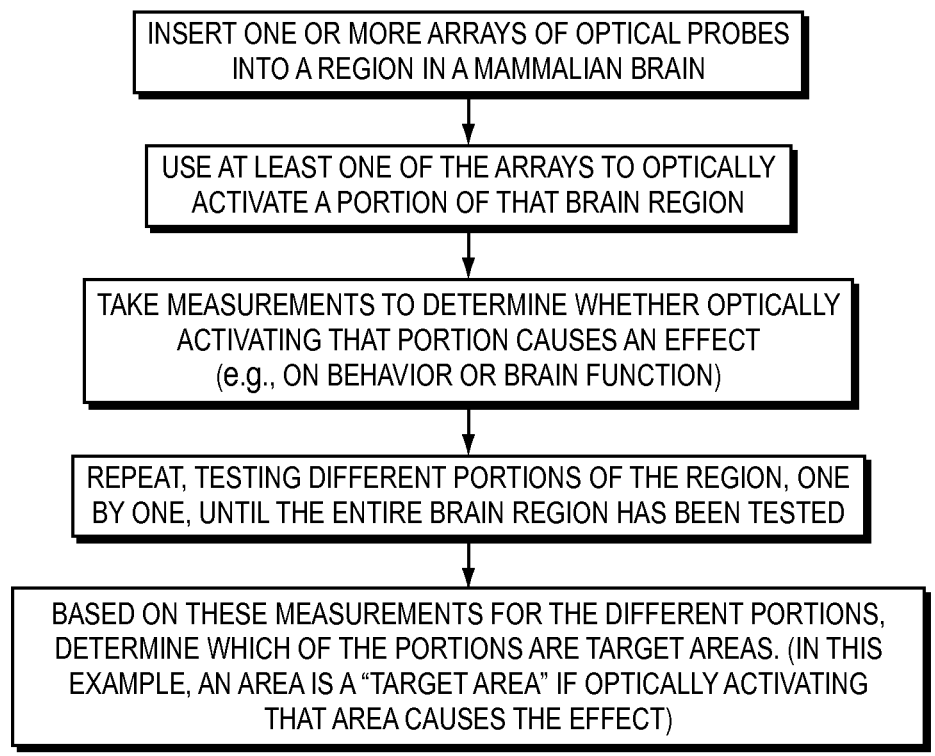
FIG. 7 is a flow chart of a serial method of neural screening pattern, in which different areas of the brain are optically activated, one by one.

FIG. 7 is a flow chart of a serial method of neural screening pattern, in which different areas of the brain are optically activated, one by one.

Figure 8:
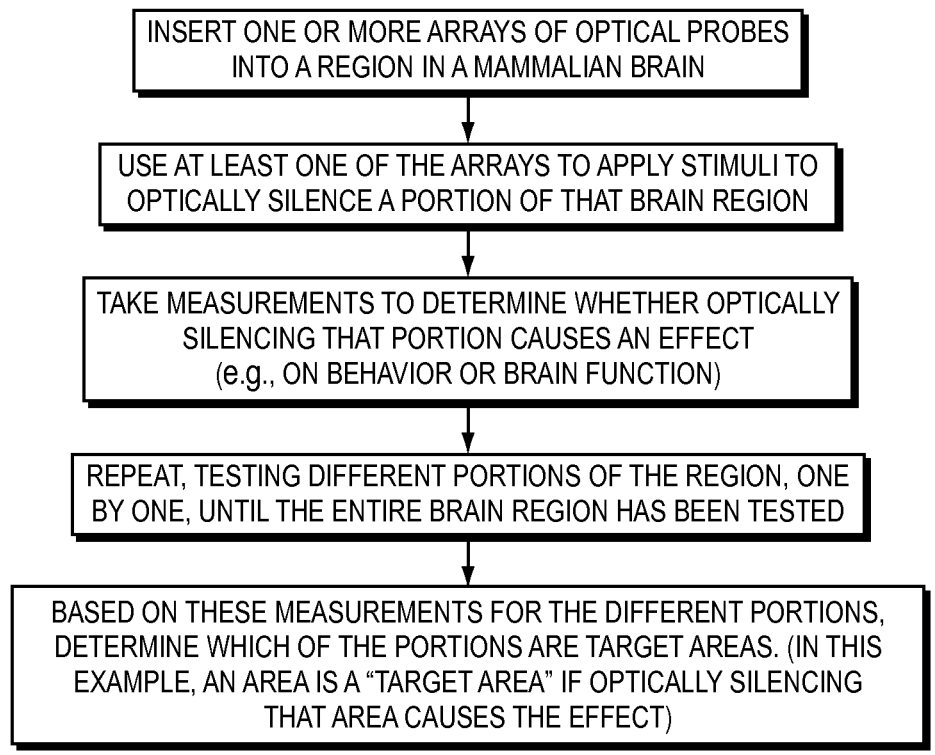
FIG. 8 is a flow chart of a serial method of neural screening pattern, in which different areas of the brain are optically silenced, one by one.

FIG. 8 is a flow chart of a serial method of neural screening pattern, in which different areas of the brain are optically silenced, one by one.

Figure 9:
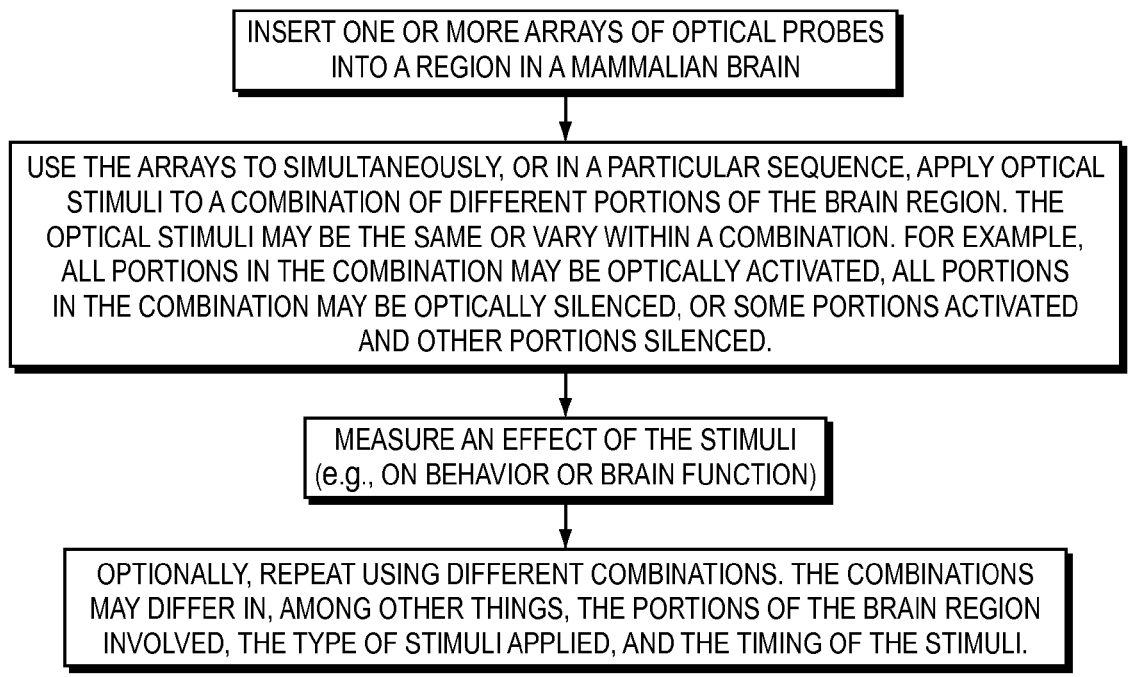
FIG. 9 is a flow chart of a combinatorial method of neural screening pattern, in which different combinations of areas of the brain are optically activated or optically silenced.

FIG. 9 is a flow chart of a combinatorial method of neural screening pattern, in which different combinations of areas of the brain are optically activated or optically silenced.

In exemplary implementations, implanted arrays may be used to probe the behavior of neural circuits, screen for the neural substrates of complex behaviors, and rectify pathological neural activity. For example, the implanted arrays of lightguides may be used to rapidly screen for neural pathology modulating targets, to identify optimal targets for serving as neuromodulatory targets to improve clinical state by altering neural activity.

According to principles of this invention, light-sensitive membrane proteins such as the depolarizing cation channel Channelrhodopsin-2 (here abbreviated ChR2) and the hyperpolarizing ion pumps Halorhodopsin and its derivatives and Archaerhodopsin (here abbreviated Arch), may be used to activate or silence neurons with millisecond timescale precision. These proteins may be selectively expressed in neural populations defined by neuroanatomical boundaries, cell types, pathways, and activation patterns through standard viral or transgenic methods, enabling precise bidirectional control of defined neural circuit elements on the timescale of neural computation.

In exemplary implementations of this invention, assays may be performed with subjects that may move freely within a behavioral arena. This is advantageous, because many cognitive functions in rodents, such as emotion, attention, working memory, and spatial learning, are assessed through behaviors which require the animal to have free movement throughout a behavioral arena.

In exemplary implementations of this invention, readout is used simultaneously with the lightguide arrays to probe the effect of optical modulation on neural circuits. Different types of readout may be used. Here are three examples: First, behavioral monitoring technologies, including real-time automated behavioral classification algorithms, can be used to gauge the net effect of optical perturbation on behaviors of interest. Second, electrophysiological recording, using probes such as tetrodes, microwire arrays, or linear electrode arrays, can measure the response of individual neurons and large neural ensembles which receive direct optical perturbation or participate in the same neural circuit as optically perturbed circuit elements. Third, whole-brain imaging methods such as fMRI and PET, which may necessitate head-fixation to resolve images taken over long timescales, may nevertheless utilize the multisite 3-dimensionality of the lightguide arrays to assess brain-wide responses to perturbation of specific neural circuit elements, as well as generate lists of targets which respond to certain perturbations, for potential screening in relation to behaviors known to rely on specific neural circuit elements.

In some implementations of this invention, readouts are performed in real time and used to achieve closed-loop control of neural circuits, triggering patterns of neural modulation based off of real-time readouts.

The neural screening may be automated. This automation improves ease of use and significantly speeds time-consuming processes, contributing to the scalability of the methods which rely on screening large numbers of neural circuit elements, timepoints, and combinations of optical modulation.

In illustrative implementations of this invention, 3-dimensional arrays of lightguides are used to optically perturb target anatomical regions of a mammalian brain containing neural circuit elements of interest.

According to principles of this invention, neural circuit elements may be targeted to express light-activated membrane proteins in a number of ways. Viral vectors (such as lentiviruses, adeno-associated viruses (AAVs), and herpes-simplex virus (HSVs)) containing a DNA payload encoding for the desired protein, may be injected directly into neuoranatomical regions of interest. Neuroanatomical boundaries such as white matter tracts often limit the spread of viral particles, resulting in the expression of light-activated membrane proteins exclusively in neuroanatomical regions of interest. Activation of specific neuroanatomical regions can also be achieved by limiting the number of injected viral particles to restrict expression of light-activated membrane proteins within a chosen radius from the injection site, or limiting the power of optical sources inserted in the brain so that light levels outside the region of interest are not great enough to excite the light-activated membrane proteins. Cell-type specificity for expression of light-activated membrane proteins may be achieved by inclusion of the appropriate promoter upstream of the code for the protein in the DNA payload of the viral vector. Transgenic mice may also be produced to express light-activated membrane proteins under specific promoters. Alternatively, transgenic mice expressing Cre-recombinase under specific promoters may be injected with virus in which the DNA encoding for light-activated membrane proteins is flanked by lox-p sites and inserted backwards into the DNA payload, such that only cells expressing Cre-recombinase cleave the DNA at the lox-p sites and reverse the orientation of the DNA for the light-activated membrane protein. Additionally, pathways between neural circuit elements may be selectively targeted by injecting viruses which travel through anterograde or retrograde connections, such as viruses containing the rabies coat protein. Or viruses may be injected in one region of the brain, but their axon terminals may be stimulated in another region of the brain, such that only connections between the circuit elements in those two regions are targeted. Additionally, expressing light-activated membrane proteins under promoters for immediate early genes such as c-fos may be used to selectively target neural circuit elements which display specific patterns of activity that result in the expression of immediate early genes.

Surgery may be performed under general anesthesia to inject virus into a brain region containing a neural circuit element of interest. For example, the surgery may be performed as follows: An incision is made in the skin on top of the head, the location of the region is determined by landmarks on the skull and stereotaxic coordinates derived from a brain atlas, a craniotomy (often ~300 microns wide, but may be many millimeters wide) is drilled into the skull, a needle (~200 micron diameter) containing virus (often ~1 microliter, but volumes from 0.5-5 microliters may be feasible) is lowered into the brain to reach the target brain region, and the virus is slowly (over the course of ~10-20 minutes) injected into the brain with the aid of a syringe pump connected to the needle through tubing containing an incompressible liquid such as silicone oil. To implant a lightguide array, a similar surgery (or an adjunct to the same surgery) is performed in which craniotomies are drilled into the skull to allow entrance for the lightguides, and the lightguide array is lowered into place on a stereotaxic arm. The array is cemented to the skull via several small screws implanted in the skull around the lightguide array.

In illustrative implementations of this invention, lightguide arrays may be powered and controlled with wired or wireless circuitry, programmed with a simple interface. When used in a wired configuration, a system of pulleys can be used to counterbalance the added weight of the wires to keep the mouse unencumbered. This system may also include a commutator to allow the mouse to freely turn in the behavioral arena without twisting the cables it is attached to. These cables may include fluid cooling lines to prevent heat produced by light sources in the arrays from detrimentally heating the mouse skull; however, sufficiently short activation paradigms do not require such cooling.

In some implementations in which the lightguides are optical fibers and the light source is an LED, it is desirable for the termini of the optical fibers to be packed more tightly in the horizontal stereotaxic plane than the raw LED die diameter: This tighter packing may be achieved, for example, by: (a) angling the optical fibers with respect to the dorsoventral axis to permit vertical stacking of the fiber termini, (b) attaching fibers off-center to the LEDs to permit dense packing of fibers, or (c) coupling two fibers to one LED to permit locally dense packing of fibers which share a single pattern of illumination.

Behavioral monitoring of animals receiving optical perturbation may be performed by a human or by behavioral classification algorithms on a computer with a video recording or live feed of the animal. Electrophysiological recording with various probes such as tetrodes, microwire arrays, and linear electrode arrays may be performed with simultaneous optical perturbation. Custom cabling and special care for electrical shielding may be necessary Whole-brain imaging may also be achieved with fMRI or PET. In this case, the lightguide array may extend over many meters, with the light generation far from the scanning equipment to avoid material incompatibility and scanning artifacts, and the lightguides may be secured within the brain during the period of the scan by means of cannulas implanted in the brain to house the lightguides.

The screening may be used to identify neural substrates of a behavior. For example, an animal may be trained to perform a task such as running through a maze to gain a reward whose location is signaled by various cues that the animal must correctly interpret. Inactivating various neural circuit elements at various timepoints in the behavior may uncover when specific neural circuit elements are necessary to complete the task, by quantifying changes in the animal's success at the task. Additionally, untrained behaviors, such as the natural fearful response to a painful stimulus, may be similarly screened for their necessary neural substrates. Additionally, neural circuit elements may be stimulated to discover when specific neural circuit elements are sufficient to complete a task.

For example, in a prototype of this invention, pyramidal neurons in the mouse infralimbic cortex were stimulated after onset of a fear-conditioned stimulus in order to extinguish the fear (as indicated by the percent of time spent freezing)

In illustrative implementations of this invention, n fibers (or waveguides with n apertures) are inserted into the brain, and then turned on one by one, or in combinations, to identify the neural targets that are most important to achieve a defined outcome (e.g. the enhancement of a memory). This high-throughput screening method allows rapid determination of which brain regions are necessary or sufficient for a behavior, or the brain regions that are most important for a given drug or other modulatory action.

The neural circuit elements screened may be chosen in a unbiased, random fashion, or they may be chosen based off of functional or anatomical evidence that they may be involved in the behavior. Furthermore, animals may be functionally imaged in a whole brain scanner such as fMRI or PET in a headfixed version of certain behaviors to generate a list of circuit elements for screening based on which regions of the brain because unusually active or inactive during the task. Alternatively, neural circuit elements known to be involved in the behavior may be stimulated while the animal is in the scanner, and brain regions that respond to the stimulation may be chosen for neural circuit screening in the freely moving task.

Paradigms for neural circuit element activation or inhibition may be chosen at random, or in graded levels of intensity at important times during a behavior. Additionally, electrophysiological recording may be used to discover correlations between activity of specific neural circuit elements and behavior. These patterns of activity can be enforced or disrupted with optical perturbation to establish causal roles in the behavior.

The activity of neural circuits may be similarly screened by activating or silencing many neural circuit elements, independently or in combination. Readout of the neural circuit activity may be achieved with electrophysiological recording or whole-brain scanning Screens of behavior or neural circuit activity may be performed in conjunction with the administration of pharmacological agents, to screen for the neural substrates which the pharmacological agent affects.

Many animals may be screened in parallel, to increase the number of neural circuit elements which can be screened and to increase the statistical significance of findings from the screen. Technologies enabling parallel animal screening include scalable behavioral controllers and tools to speed up implantation of lightguide arrays. Wireless controllers and power sources may address many animals at the same time. Tools to parallelize craniotomies, or automatically drill craniotomies through a computer-controlled mill may be used to dramatically increase the speed of implantation surgeries. For example, a parallelized craniotomy marker may be used. This marker may comprise hollow 32 gauge hypodermic tubing, with ink on the ends of the tubing.

Advantages and Applications

This invention has many practical applications, and many advantages over conventional approaches. Here are some examples:

In exemplary implementations of this invention, high-throughput neural screening is performed by independent optical modulation of many sites in the brain for use with freely moving rodents. In contrast, a conventional approach utilizes a cannula in which a optical fiber is inserted for the duration of an experiment; the optical fiber is coupled to a laser at least several feet away from the mouse head. This conventional method does not scale to multiple sites in freely moving rodents because of the danger of tangling stiff glass optical fibers, which cannot be commutated in the manner that the present invention commutates electrical power lines.

In exemplary implementations of this invention, multisite optical modulation allows the rapid screening of many circuit elements to determine which elements are involved in a particular behavior or neural computation, probe the consequences of interactions between circuit elements which cannot be predicted from the response of each element to independent perturbation, and address large brain structures (e.g. the hippocampus) which extend beyond the volume of neural tissue which can be activated by a single light source in the brain (without emitting so much power from the light source that detrimental heating of tissue occurs. It is possible to insert multiple optical fibers into a headfixed rodent. However, many important cognitive functions in rodents, such as emotion, attention, working memory, and spatial learning, are assessed through behaviors which require the animal to have free movement throughout a behavioral arena. Exemplary embodiments of the present invention allow assays while the animal has free movement in a behavioral arena, which is highly advantageous.

Additionally, the LED light sources used in a prototype of this invention, which cost ~$1 each, are significantly cheaper than commercial lasers, which cost hundreds to thousands of dollars each.

Conventional methods of neural circuit screening, whether using light-activated membrane proteins or other methods such as mechanical and pharmacological lesioning, are prohibitively laborious, as only one neural circuit element can typically be screened in each animal, and so large-scale or unbiased screens of the neural substrates of complex behaviors are rarely if ever undertaken.

In contrast, neural screening in accordance with this invention can increase the chances of discovering unexpected participation of overlooked neural circuit elements in many behaviors. These elements may be overlooked in conventional methods, because conventional techniques are so laborious and expensive that they tend to discourage looking for the contribution of neural circuit elements which are thought not to play any role in the functioning of behavior.

In some implementations of this invention, neural screening is performed rapidly in vivo in the animal brain, to find the brain circuits that, when manipulated, yield the best therapeutic value—remedying the behavioral or therapeutic dysfunction, to improve the clinical scenario. Thus, neuromodulation targets (such as those that could be used for deep brain stimulation) can be rapidly screened. This could yield new neural targets for depression, obsessive compulsive disorders, Parkinsons, epilepsy, etc.

In some implementations, neural screening is used not only to identify neural targets, but also to evaluate which pulse sequences are optimal. This may be used to optimize neuromodulation. For example, with a large number of animals connected to wireless power and wireless control, circuits may be activated and shutdown remotely, in a high-throughput fashion, on a large number of mice, rapidly identifying key neural targets, as well as pulse sequences at these targets. For example, different animals may receive different pulse sequences, at different targets, triggered at different times. Thus, in illustrative implementations, this invention may be used for "high-throughput screening" of targets and algorithms for manipulating those targets.

In some implementations of this invention, neural screening is used to find where in the brain a drug acts, by administering a drug to an animal (e.g., systemically) and then shutting down brain structures until the effect of the drug disappears, either in main effect or side effect.

In some implementations of this invention, neural screening is used to find targets for neural prosthetics.

Variants

This invention may be implemented in many different ways. Here are a few examples:

In some implementations of this invention, 3-dimensional light guide arrays are implanted in, or on top of, or adjacent to, a mammalian brain to perturb defined neural circuit elements to screen for their role in a mammal's behavior. Also, for any of these implementations, one or more of the following may apply: (1) neural circuit elements may be defined by neuroanatomical boundaries, cell types, pathways, or activity patterns, (2) three-dimensional light guides may comprise 2-dimensional arrays of optical fibers coupled to LEDs, (3) three-dimensional light guides may comprise 2-dimensional arrays of optical probes consisting of a number of waveguides terminating along the length of the probe within the brain, coupled to lasers or LEDs outside the brain, (4) trained behaviors may be assayed, (5) behaviors may comprise the untrained, natural activity of subjects, (6) behaviors may be caused by pathological neurological activity, (7) behaviors may be performed in conjunction with administration of pharmacological agents, (8) behavior may be measured through visual analysis (e.g., by a machine vision algorithm), (9) behavior may be measured by electrophysiological measurements of neurological activity (10) electrophysiological measurements may be made with one or several linear electrode arrays, (11) electrophysiological measurements may be made with one or several tetrodes, (12) electrophysiological measurements may be made with one or several microwires, (13) electrophysiological measurements may be made with screws implanted in the skull, (14) electrophysiological measurements may be made with non-invasive electroencephalography (EEG) electrodes attached to the head, (15) behavior may be measured by electromyography (EMG), (16) behavior may be measured by whole-brain imaging (15) whole-brain imaging may be performed with functional magnetic resonance imaging (fMRI), (16) whole-brain imaging may be performed with positron emission tomography (PET), (17) defined neural circuits may be chosen at random, (18) defined neural circuits may be chosen from whole brain imaging of a mammal engaging in the behavior, (19) defined neural circuits may be chosen from whole brain imaging of a mammal undergoing neural circuit perturbation, (20) the neural circuit perturbation may be electrical stimulation, (21) the neural circuit perturbation may be optical stimulation or inhibition, (22) the neural circuit perturbation may be administration of a pharmacological agent, (23) defined neural circuits may be individually inhibited to screen for necessity in a behavior, (24) defined neural circuits may be combinatorially inhibited to screen for interactions between regions, (25) inhibition may be applied throughout the entire course of the behavior, (26) inhibition may be applied at specific time points in the course of the behavior, (e.g., for periods of milliseconds to seconds), (27) inhibition may be triggered by predefined electrophysiological signals, (28) inhibition may be triggered by predefined actions of the subject, (29) defined neural circuits may be individually stimulated with trains of light pulses to screen for sufficiency in a behavior, (30) defined neural circuits may be combinatorially stimulated with trains of light pulses to screen for interactions in a behavior, (31) light pulses may be applied at specific time points in the course of the behavior, (32) light pulses may be triggered by predefined electrophysiological signals, and (33) light pulses may be triggered by predefined actions of the subject.

This invention may be implemented as a method which comprises, in combination, the steps of: (a) inserting one or more arrays of optical probes into a mammalian brain, or positioning the one or more arrays adjacent to the brain, (b) using the arrays to optically silence all of a region of the brain, (c) taking measurements to determine whether optically silencing all of the region produces a specified outcome, (d) if the effect is observed, using at least some of the arrays to optically silence subregions of that region, one subregion at a time, (e) for each particular subregion in that set, taking measurements to determine whether optically silencing that particular subregion produces the specified outcome, and (f) repeating the preceding two steps iteratively for progressively smaller subdivisions, wherein the steps listed above occur in a chronological order, which chronological order may be the same or different than the order in which listed above. Furthermore: (1) the one or more arrays may be adapted to deliver, when implanted in a particular location in the brain, light to multiple points in a three-dimensional volume of the brain, (2) each of the one or more arrays may be adapted to deliver light of one color to at least one point in the brain and to simultaneously deliver light of at least one other color to at least one other point in the brain, (3) the one or more arrays may each be adapted to deliver light to modulate the activity of light-sensitive proteins in neural tissue, and (4) the light-sensitive proteins may comprise one or more rhodopsins.

This invention may be implemented as a method which comprises, in combination, the steps of: (a) inserting one or more arrays of optical probes into a mammalian brain, or positioning the one or more arrays adjacent to the brain, (b) using at least one of the arrays to deliver optical stimulation to a region of the brain, (c) taking measurements to determine whether delivering the optical stimulation to that region produces a specified outcome, and (d) repeating the preceding two steps, applying the optical stimulation to different regions of the brain, one region at a time, wherein the steps listed above occur in a chronological order, which chronological order may be the same or different than the order in which listed above. Furthermore: (1) the optical stimulation, when delivered to an area of the brain, may activate that area, (2) the optical stimulation, when delivered to a specified area of the brain, may silence that specified area, (3) each of the one or more arrays may be adapted to deliver, when implanted in a particular location in the brain, optical stimulation to multiple points in a three-dimensional volume of the brain, (4) each of the one or more arrays may be adapted to deliver light of one color to at least one point in the brain and to simultaneously deliver light of at least one other color to at least one other point in the brain, (5) the one or more arrays may each be adapted to deliver light to modulate the activity of particular light-sensitive proteins in neural tissue, (6) the particular light-sensitive proteins may comprise one or more rhodopsins, and (7), if any overlap volumes do exist, in which any of the respective different regions overlaps with any of its respective neighbors, then ratio of the overlap volumes (without any double counting) to the total volume of the different regions together, may be less than 30%.

This invention may be implemented as a method which comprises, in combination, the steps of: (a) inserting one or more arrays of optical probes into a mammalian brain, or locating the one or more arrays adjacent to the brain, (b) using at least one of the arrays to simultaneously, or in a particular sequence, deliver optical stimuli to a combination of different regions in the brain, which optical stimuli may be the same or vary within or between the different regions, and (c) taking measurements to determine the optical stimuli produces a specified outcome, wherein the steps listed above occur in a chronological order, which chronological order may be the same or different than the order in which listed above. Furthermore: (1) the last two steps (delivering the optical stimuli and taking the measurements) may be repeated for different combinations of regions in the brain, (2) these last two steps may be repeated for the same combination of regions of the brain, but one or more of the type and timing of optical stimuli that is delivered at particular locations in the brain may vary between different repetitions, (3) each of the one or more arrays may be adapted to deliver, when implanted in a particular location in the brain, optical stimulation to multiple points in a three-dimensional volume of the brain, (4) each of the one or more arrays may be adapted to deliver light of one color to at least one point in the brain and to simultaneously deliver light of at least one other color to at least one other point in the brain, (5) the one or more arrays may each be adapted to deliver light to modulate the activity of light-sensitive proteins in neural tissue, and (6) the light-sensitive proteins may comprise one or more rhodopsins.

CONCLUSION

It is to be understood that the methods and apparatus which have been described above are merely illustrative applications of the principles of the invention. Numerous modifications may be made by those skilled in the art without departing from the scope of the invention. The scope of the invention is not to be limited except by the claims that follow.

What is claimed is:
1. A method which comprises, in combination, the steps of:
(a) inserting one or more arrays of optical probes into a mammalian brain, or positioning the one or more arrays adjacent to the brain;
(b) using the arrays to optically silence all of a region of the brain;
(c) taking measurements using a sensor to determine whether optically silencing all of the region produces a specified outcome;
(d) if the specified outcome is observed, using at least some of the arrays to optically silence subregions of that region, one subregion at a time;
(e) for each particular subregion in that set, taking measurements to determine whether optically silencing that particular subregion produces the specified outcome; and

(f) repeating the preceding two steps iteratively for progressively smaller subdivisions;

wherein the steps listed above occur in a chronological order, which chronological order may be the same or different than the order in which listed above.

2. The method of claim 1, wherein each of the one or more arrays is adapted to deliver, when inserted in a particular location in the brain, light to multiple points in a three-dimensional volume of the brain.

3. The method of claim 1, wherein each of the one or more arrays is adapted to deliver light of one color to at least one point in the brain and to simultaneously deliver light of at least one other color to at least one other point in the brain.

4. The method of claim 1, wherein the one or more arrays are each adapted to deliver light to modulate the activity of light-sensitive proteins in neural tissue.

5. The method of claim 4, wherein the light-sensitive proteins comprise one or more rhodopsins.

6. A method which comprises, in combination, the steps of:
(a) inserting one or more arrays of optical probes into a brain of a mammal, or positioning the one or more arrays adjacent to the brain;
(b) using at least one of the arrays to deliver optical stimulation to a region of the brain;
(c) using a sensor to take measurements regarding the mammal or the mammal's behavior; and
(d) repeating the preceding two steps, applying the optical stimulation to different regions of the brain, one region at a time;
wherein
(i) the steps listed above occur in a chronological order, which chronological order may be the same or different than the order in which listed above;
(ii) the one or more arrays are each adapted to deliver light to modulate the activity of particular light-sensitive proteins in neural tissue; and
(iii) the particular light-sensitive proteins comprise one or more rhodopsins.

7. A method which comprises, in combination, the steps of:
(a) inserting one or more arrays of optical probes into a brain of a mammal, or positioning the one or more arrays adjacent to the brain;
(b) using at least one of the arrays to deliver optical stimulation to a region of the brain;
(c) using a sensor to take measurements regarding the mammal or the mammal's behavior; and
(d) repeating the preceding two steps, applying the optical stimulation to different regions of the brain, one region at a time;
wherein
(i) the steps listed above occur in a chronological order, which chronological order may be the same or different than the order in which listed above; and
(ii) if any overlap volumes do exist, in which any of the respective different regions overlaps with any of its respective neighbors, then ratio of the overlap volumes without any double counting to the total volume of the different regions together, is less than 30%.

8. A method which comprises, in combination, the steps of:
(a) inserting one or more arrays of optical probes into a brain of a mammal, or locating the one or more arrays adjacent to the brain;
(b) using at least one of the arrays to simultaneously deliver optical stimuli to a combination of different regions in the brain, which optical stimuli may be the same or vary within or between the different regions; and
(c) using a sensor to take measurements regarding the mammal or the mammal's behavior;
wherein
(i) the steps listed above occur in a chronological order, which chronological order may be the same or different than the order in which listed above,
(ii) the one or more arrays are each adapted to deliver light to modulate the activity of particular light-sensitive proteins in neural tissue, and
(iii) the light-sensitive proteins comprise one or more rhodopsins.

\* \* \* \* \*